(12) United States Patent
Wang et al.

(10) Patent No.: US 8,472,795 B2
(45) Date of Patent: Jun. 25, 2013

(54) SYSTEM AND METHOD FOR CAPSULE CAMERA WITH ON-BOARD STORAGE

(75) Inventors: Kang-Huai Wang, Saratoga, CA (US); Gordon C Wilson, San Francisco, CA (US)

(73) Assignee: Capso Vision, Inc, Saratoga, CA (US)

( * ) Notice: Subject to any disclaimer, the term of this patent is extended or adjusted under 35 U.S.C. 154(b) by 64 days.

(21) Appl. No.: 13/115,920

(22) Filed: May 25, 2011

(65) Prior Publication Data

US 2012/0301124 A1 Nov. 29, 2012
US 2013/0129334 A9 May 23, 2013

Related U.S. Application Data

(63) Continuation-in-part of application No. 11/533,304, filed on Sep. 19, 2006, now Pat. No. 7,983,458.

(51) Int. Cl.
*G03B 41/00* (2006.01)

(52) U.S. Cl.
USPC .......................................................... 396/14

(58) Field of Classification Search
USPC .......................................................... 396/14
See application file for complete search history.

(56) References Cited

U.S. PATENT DOCUMENTS

| | | | |
|---|---|---|---|
| 6,645,832 B2 * | 11/2003 | Kim et al. | 438/456 |
| 2002/0198439 A1 * | 12/2002 | Mizuno | 600/109 |
| 2003/0153122 A1 * | 8/2003 | Brooks | 438/107 |
| 2004/0027459 A1 * | 2/2004 | Segawa et al. | 348/207.99 |
| 2004/0113256 A1 * | 6/2004 | Thomas et al. | 257/686 |
| 2005/0049461 A1 * | 3/2005 | Honda et al. | 600/160 |
| 2005/0054901 A1 * | 3/2005 | Yoshino | 600/176 |
| 2006/0073635 A1 * | 4/2006 | Su et al. | 438/109 |
| 2006/0249737 A1 * | 11/2006 | Fujimori | 257/79 |
| 2007/0098379 A1 | 5/2007 | Wang et al. | |
| 2009/0161402 A1 * | 6/2009 | Oh et al. | 365/51 |
| 2010/0244212 A1 * | 9/2010 | Ha et al. | 257/676 |

* cited by examiner

*Primary Examiner* — W B Perkey
(74) *Attorney, Agent, or Firm* — Blairtech Solution LLC

(57) ABSTRACT

A capsule camera with on-board storage to archive the captured images in on-board non-volatile memory is disclosed. The capsule camera with on-board storage comprises multiple chips including a system processing chip and one or more non-volatile memory chips, where the system processing chip includes a compression module to compress images captured. If the multiple chips use individual chip packages and are disposed on respective printed circuit boards according to a conventional approach, it would require too much space to fit the multiple chips into the capsule camera housing. Accordingly, a capsule camera embodying the present invention is disclosed where the capsule camera integrates an image sensor, a light source, at least one system processing chip comprising compression module, one or more non-volatile memory chips and a battery into a housing, wherein the at least one system processing chip and said one or more non-volatile memory chips are disposed vertically in a multiple chip assembly.

25 Claims, 9 Drawing Sheets

SYSTEM AND METHOD FOR CAPSULE CAMERA WITH ON-BOARD STORAGE

CROSS REFERENCE TO RELATED APPLICATIONS

The present invention is continuation-in-part of U.S. patent application Ser. No. 11/533,304, entitled "In Vivo Autonomous Camera with On-Board Data Storage or Digital Wireless Transmission in Regulatory Approved Band", filed on Sep. 19, 2006. The U.S. Non-Provisional Patent Application is hereby incorporated by reference in its entirety.

FIELD OF THE INVENTION

The present invention relates to diagnostic imaging inside the human body. In particular, the present invention relates to multi-chip packaging for a capsule camera having on-board storage.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule. The wireless-based capsule camera system will require a patient to wear a wireless transceiver and data recorder to receive and record the captured images. The capsule camera may stay in the body for over ten hours. Therefore, the patient may have to wear the wireless data receiver pack for extended hours which may be uncomfortable.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. The capsule camera with on-board storage archives the captured images in on-board non-volatile memory. The capsule camera is retrieved upon its exiting from the human body. The images stored in the non-volatile memory of the retrieved capsule camera is then accessed through an output port on in the capsule camera. The images can be processed and displayed on viewing station and examined by diagnostician. In order to reduce the required storage space, the images captured usually are compressed using image/video compression. On the other hand, the capsule camera has to provide sufficient storage capacity for the captured. The on-board storage has to be able to retain the captured image data for a period of time without any power supplied. Therefore, non-volatile memory has to be used for on-board storage. The total number of stored images may be quite large and there is a trend of demanding for higher resolution in order to provide more accurate diagnosis based on images with more details. Therefore, multiple non-volatile memory chips may be required to fulfill the storage capacity requirement. Besides the multiple non-volatile memory chips required, the system may also include multiple processing chips to perform various tasks such as motion metric evaluation, image/video compression, and system control. Therefore, a capsule camera with on-board storage faces the challenge to pack multiple chips and various components such as sensor, LED light source, batteries into the capsule camera housing. It is very desirable to pack the multiple chips in a compact means to make the capsule camera as small as possible for easy to swallow.

DETAILED DESCRIPTION OF THE INVENTION

Semiconductor memories are low-cost, low-power, easily available from multiple sources, and compatible with application specific integrated circuit (ASIC) and sensor electronics (i.e., the data sources), and a personal computer (i.e., the data destination) without format conversion devices. One embodiment of the present invention allows images to be stored in an "on-board storage" using semiconductor memories. The capsule camera disclosed in U.S. patent application Ser. No. 11/533,304, entitled "In Vivo Autonomous Camera with On-Board Data Storage or Digital Wireless Transmission in Regulatory Approved Band", filed on Sep. 19, 2006, comprises image compression processor and on-board storage to store compressed images for the configuration with on-board storage. While the U.S. patent application Ser. No. 11/533,304, discloses image compression to reduce storage requirement, other compression techniques such as motion-compensated video compression may also use to substantially reduce the storage requirement. On the other hand, the U.S. patent application Ser. No. 11/533,304, discloses various processing modules for the capsule camera to capture images for storage, such as motion detection and motion metric evaluation. Nevertheless, the present invention is not limited to the specific implementation of the processing described in the U.S. patent application Ser. No. 11/533,304. Instead, the present invention addresses components packaging for capsule camera with on-board storage, where the components comprise at least one non-volatile memory chip and at least one system processing chip associated with image/video compression. In this disclosure the terms "capsule" and "capsule camera" are interchangeable. Also the terms "capsule system" and "capsule camera system" are interchangeable. While the term "chip" may refer to a "bare chip" (i.e., die) or a "chip with a chip package" in the field, the term "chip" refers to a "bare chip" in this disclosure.

Figure 1:
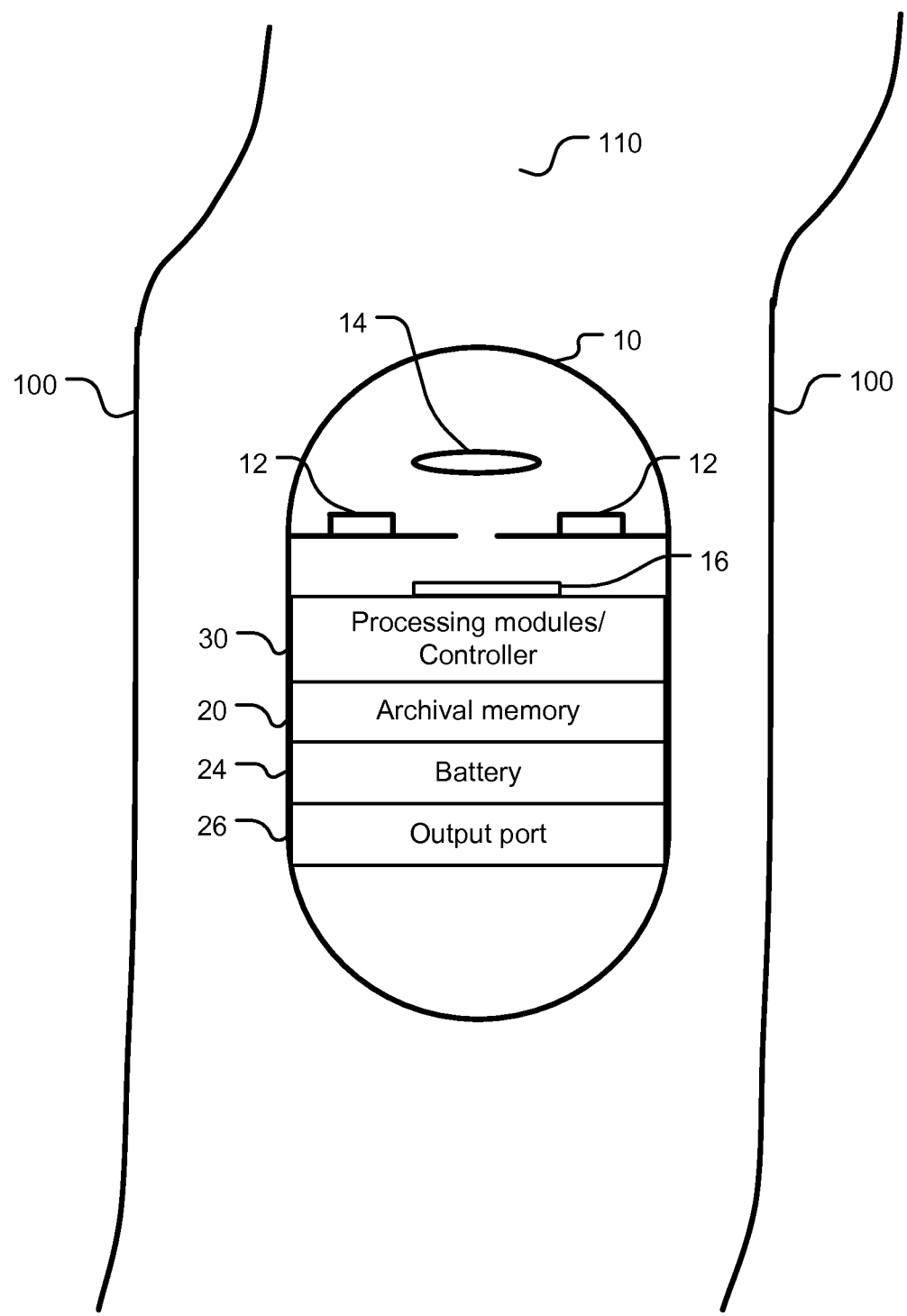
FIG. 1 illustrates one example of the capsule camera system having on-board storage.

FIG. 1 shows a swallowable capsule system 110 inside body lumen 100, in accordance with one embodiment. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 100 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is made of non-toxic material, and is sufficiently smooth to minimize the chance of lodging within the lumen.

As shown in FIG. 1, capsule system 110 includes illuminating system 12 and a camera that includes optical system 14 and image sensor 16. The system may include processing modules/controller 30 to perform various tasks such as sensor image processing, motion metric evaluation, image/video compression and system control. A semiconductor nonvolatile archival memory 20 may be provided to allow the images to be stored on-board and retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16.

Archival memory system 20 can be implemented by one or more nonvolatile semiconductor memory devices. Since the image data are digitized for digital image processing techniques, such as motion detection, memory technologies that are compatible with digital data are selected. Of course, semiconductor memories mass-produced using planar technology is the most convenient. Such memories are low-cost and may be obtained from multiple sources. Semiconductor memories are most compatible because they share common power supply with the sensors and other circuits in capsule system 110, and require little or no data conversion when interfaced with an upload device at output port 26. Archival memory system 20 preserves the data collected during the operation, after the operation while the capsule is in the body, and after the capsule has left the body, up to the time the data is uploaded. This period of time is generally less than a few days. A nonvolatile memory is preferred because data is held without power consumption, even after the capsule's battery power has been exhausted. Suitable non-volatile memory includes flash memories, write-once memories, and electronically programmable read-once memories (EPROM). Alternatively, archival memory system 20 may be volatile and static (e.g., a static random access memory (SRAM) or its variants, such as VSRAM, PSRAM)

Archival memory 20 may be used to hold any initialization information (e.g., boot-up code and initial register values) to begin the operations of capsule system 110. The cost of a second non-volatile or flash memory may therefore be saved. That portion of the non-volatile can also be written over during operation to store the selected captured images. After the capsule passes from the body, it is retrieved. Capsule housing 10 is opened and output port 26 is connected to an upload device for transferring data to a computer workstation for storage and analysis.

Figure 2A:
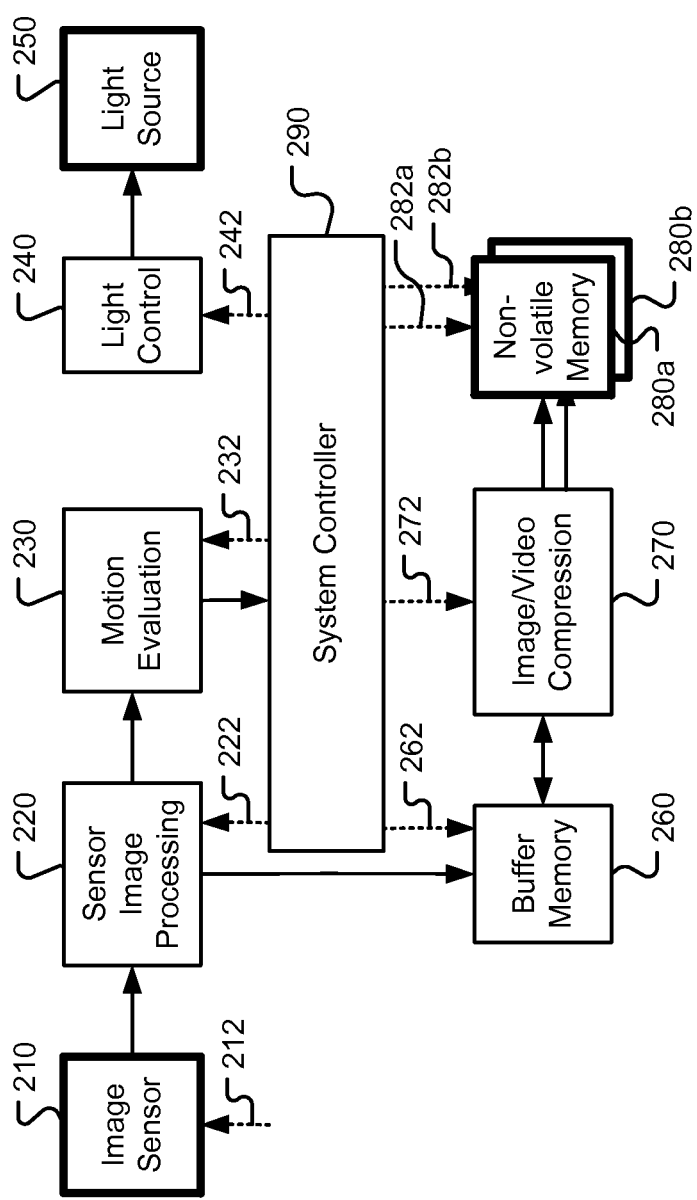
FIG. 2A illustrates an exemplary system block diagram of the capsule camera system having on-board storage.

FIG. 2A illustrates an exemplary system block diagram of a capsule camera with on-board storage. The system uses a system controller 290 to manage and coordinate overall system operations and provides necessary control signals to various system components and modules. The processing modules shown in FIG. 2A illustrate one example of system functional partition and there may be many other system partitions that may result in different processing modules. According to the arrangement shown in FIG. 2A, the image data from the image sensor 210 is provided to sensor image processing module 220, which will perform a set of image processing tasks selected from filtering, noise reduction, demosaicing, sharpening, and format conversion. The Image sensor 210 is operated by providing sensor control 212 from system controller 290. System controller 290 also provides various settings and parameter controls 222 to sensor image processing module 220. The processed image data is then provided to the motion evaluation module 230 to assess motion between a current frame and a previous frame. The motion information is used by the system to determine whether to archive the input image data in order to reduce the amount of stored image data. Motion evaluation module 230 determines whether to capture an input frame. While motion evaluation is illustrated as a means for image capture control, other means for determining the capture decision may be used. Furthermore, when motion compensated video coding is used, capture control may be inherent in the video compression. Therefore, motion evaluation may not be needed for capture control in this case. Nevertheless, motion evaluation is still useful for light source control and and/or image sensor control to conserve power. Motion evaluation may be configured by the system controller 290 through control 232 to set up parameters or to perform select tasks. Images from sensor image processing module 220 may also be routed to buffer memory 260 where a part or the whole input image may be stored. For example, eight image lines may be buffered if JPEG compression is used to compress captured images. If motion-compensated video coding is used to compress a captured image, a whole previously reconstructed image may have to be buffered in buffer memory 260. The image to be captured is then subject to image/video compression 270 and the compressed image/video data is then stored on non-volatile memories 280a and 280b. Two instances of non-volatile memories are used to illustrate the case where multiple non-volatile memory chips may be needed to provide the required storage capacity. Depending on the required archival memory space and the available capacity of the non-volatile memory, one of more non-volatile memory chips will be used in the system accordingly. System controller 290 will provide control signals 262, 282 and 282a/b to buffer memory 260, image/video compression module 270 and non-volatile memories 280a/b respectively for proper setting and control. While the non-volatile memories 280a/b are mainly intended for archiving captured image data, the non-volatile memories may also be shared by other functions, such as to store program codes to run on system controller 290 or to store system parameters or other sensor data. System controller 290 may also provide light control signal 242 to light control module 240 for controlling light source 250. While light control module 240 and light source 250 are shown separately, the light control module may be embedded into the light source assembly as a single device.

Figure 2B:
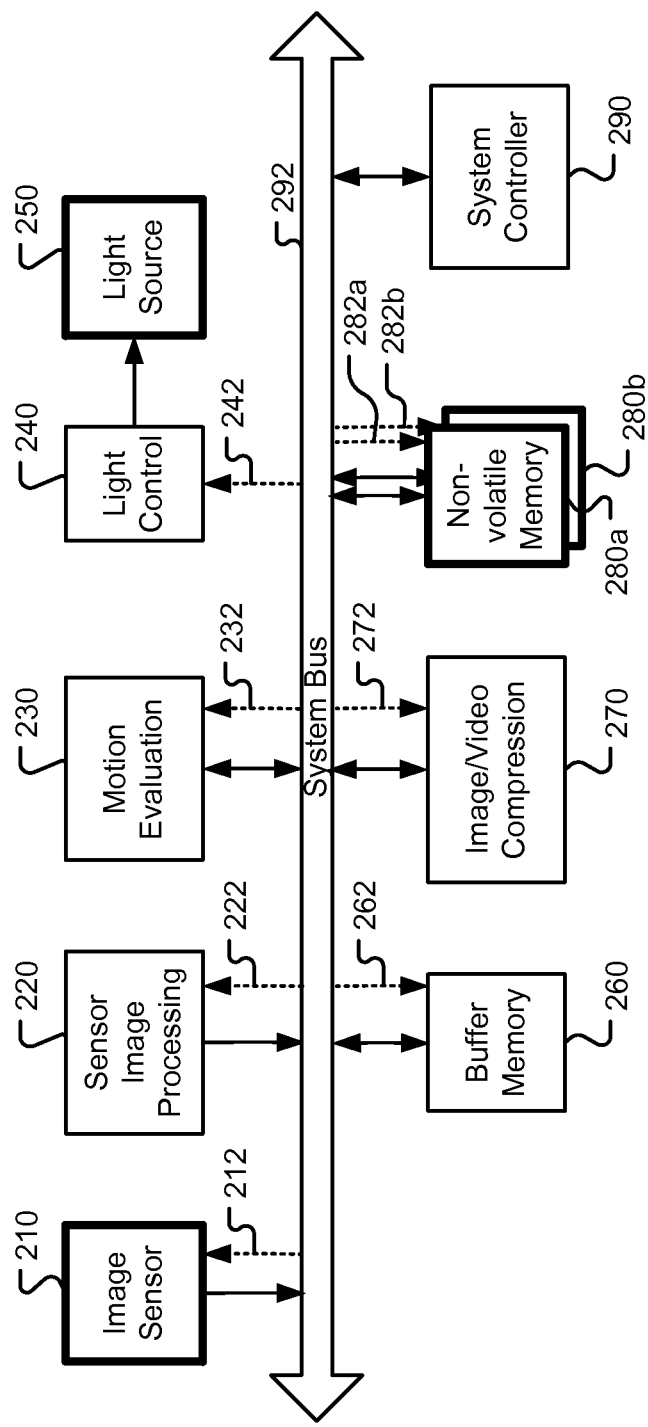
FIG. 2B illustrates an exemplary system block diagram of the capsule camera system having on-board storage, where the system adopts system bus architecture.

While FIG. 2A illustrates system architecture configured to practice capsule camera with on-board storage, other system architectures may also be used. For example, FIG. 2B illustrates alternative system architecture configured to practice the capsule camera with on-board storage where a system bus 292 is used to interconnect system modules and components. The system bus 292 usually comprises data bus and address for transport data among various processing modules and devices. Nevertheless, the address and data may share the same bus to conserve the number of interconnection wires and bond pads. In addition, the system bus may also include control bus to convey the required control signals among modules and devices. The system may be partitioned differently to implement the required processing for a capsule camera. The present invention is not limited to the particular system partition or configuration shown in FIGS. 2A and 2B.

As mentioned above, there are various functions and tasks that the capsule camera has to perform. The system may be implemented in multiple processing modules to fulfill the requirement to perform various functions and tasks. Due to the limited space within the housing, it is desirable to integrate the modules and devices as much as possible. For example, thanks to the advances in semiconductor device fabrication technology, the feature width has been continuing to shrink to allow more digital circuits put on a given die area. Therefore, it becomes possible to integrate the processing modules onto a small number of chips or even a single chip. Nevertheless, a capsule camera with on-board storage will require sizeable non-volatile memory capacity to accommodate the massive amount of image data collected. For example, if color sensor images are captured at a resolution of 288×240 pixels and JPEG compression is used to reduce the required storage, each captured image will require about 69,120 bytes for the JPEG compression with target of 1 bit/pixel. If the JPEG compression is targeted at 2 bits/pixel, each captured image will require about 138,240 bytes. During the course of examining the GI tract, the capsule camera may take tens of thousands of images. If 50,000 images are captured, it will result in about 432 million bytes data at 1 bit/pixel and about 864 million bytes data at 2 bit/pixel. As shown in the above example, the requirement of non-volatile memory for storing captured images will be substantial for capsule camera with on-board storage. Motion compensated video coding such as MPEG-2 and H.264/AVC, can achieve high efficiency compression compared with the JPEG image compression. While motion compensated video coding can substantially reduce the storage requirement, the reduced space will be claimed by the increasing spatial resolution desired by the capsule camera. Therefore, video compression combined with non-volatile memory is critical to the success of high resolution capsule camera with on-board storage. Furthermore, the use of motion compensated video coding may cause the need for a separate memory chip for the frame buffer required by motion compensated video coding.

There are various existing technologies existing today to fabricate non-volatile memory (NVM) such as Erasable Programmable Read Only Memory (EPROM), and Flash memory. There are also emerging technologies that may provide the required storage capacity, such as Magnetoresistive Random Access Memory (MRAM), and Phase-Change Memory (PRAM or PCRAM). Most NVM technologies use a different fabrication process different from the standard digital CMOS process. Therefore, there will be great technical difficulty, if it is possible, to embed the large capacity NVM for archiving thousands or tens of thousands of images on the same die of the system processing chip. There is a technology that allows the NVM embedded on a CMOS standard chip. Such technology uses antifuse technology to create a one-time programmable (OTP) memory. However, the OTP NVM implies that the capsule camera cannot be re-used. Therefore, the OTP NVM may not be a cost-effective option for the capsule camera with on-board storage. In some applications, a single NVM chip may have a die area larger than the cross section of the capsule camera and the NVM chip may not fit into the mechanical design constraints. Therefore, several NVM chips, each with smaller capacity, may have to be used instead. While the cross section area of the capsule camera is limited, the vertical space is also very limited. It may not be able to accommodate multiple chips with respective individual packages in the vertical direction according to a conventional approach.

In typical package arrangement for the capsule camera, the chips are disposed on one or more Printed Circuit Boards (PCBs) where each PCB has a diagonal dimension smaller than the inner diameter of the capsule camera housing. Interconnection cable or cables, often a flexible type, are used to interconnect the PCBs. It is also possible to use headers or other means to electrically interconnect PCBs. The PCBs with chips in respective chip packages mounted are stacked vertically with or without other components such as batteries in between to fit into the housing. In order to utilize the vertical space efficiently, the chip package may adopt micro-BGA technology with fine pitch size. As an example, a capsule camera may comprise a system processing chip in a chip package and four non-volatile memory chips in their respective chip packages. Five PCBs with the five chips would result in a very large overall height with the five PCBs interconnected. When a flex cable is used to electrically interconnect two boards, the flex cable is subject to minimum bend radius. For example, the minimum bend radius specified for a flex circuit cable with a single metal layer is 3-6 times of the circuit thickness. Therefore, the minimum space required for cable ending is 6-12 times of the circuit thickness though the flex cable is very thin. When multiple flex cables are used to electrically interconnect multiple printed circuit boards, the overall space required for flex cable bending will be substantial to prevent them from practical use in the capsule camera with on-board storage. To reduce printed circuit board thickness as well as to eliminate the need for separate connection between the flex cable and the printed circuit board, the flex cable can be made of flex circuit cable extended from a flex printed circuit board. Nevertheless, the mechanical strength of the flex board exerted will cause assembly issue. The wide flex board bus will make the available board space smaller. Furthermore, the flex printed circuit board with flex circuit cable does not solve the issue of limited overall space required by the capsule camera. A capsule camera based on multiple printed circuit boards electrically interconnected by flex cable has other complications such as lower yield associated with the reliability of multiple printed circuit boards, higher manufacturing cost as well as higher power due to parasitic capacitance. Furthermore, the longer the electrical connection lines from the battery to the devices is, the worse the ground and power stability will be. Consequently, the system failure rate will increase and image quality will be degraded by additional noises introduced. Using two-sided PCBs will help to relieve the vertical space constraint to some degree. Nevertheless this may not be good enough to make a capsule camera to compact enough for easy to swallow. It is evident that there is a need to resolve the space issue for accommodating multiple chips within the space-limited capsule camera housing.

Figure 3A:
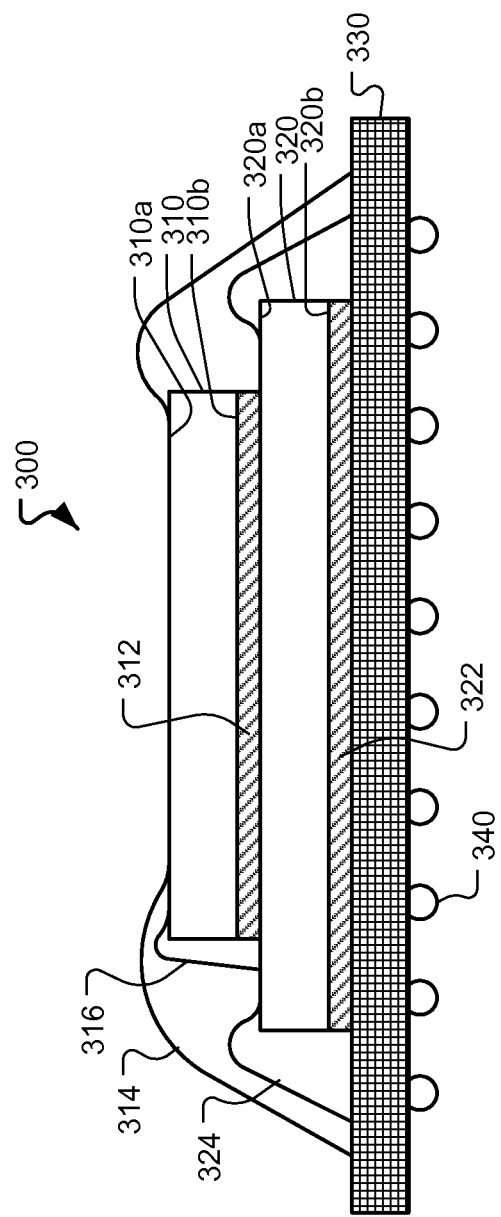
FIG. 3A illustrates an example of a stacked multiple chip package having two chips.

FIG. 3A illustrates an exemplary stacked multiple chip package (MCP) 300 containing two chips that can be used to achieve compact vertical space. Other terms for the multiple chip package are also often used in the field such as multiple chip module (MCM). First chip 310 is stacked on top of the second chip 320 vertically, where the first chip is smaller than the second chip. Each chip has a circuit surface (310*a* and 320*a*) and a non-circuit surface (310*b* and 320*b*). The non-circuit surface of the first chip is attached to the circuit surface of the second chip using die bonding layer 312. Die bonding material may be, for example, a conductive epoxy, non-conductive epoxy, bonding tape and other similar materials. The circuit surface contains bonding pads (not shown in the drawing) that electrically connect internal circuits of the respective chip to external circuits. Since the first chip 310 is smaller than the second chip 320, there will be some area on the circuit surface 320*a* of the second chip 320 to expose the bonding pads fabricated on the circuit surface. The non-circuit surface 320*b* of the second chip 320 is attached to the top side of substrate 330 using die bonding layer 322. Various substrates may be used to practice the present invention such as ceramic and glass ceramic substrates, organic substrate, and flex substrate. On the top side of the substrate 330, bond fingers (not shown) are provided and solder balls 340 are disposed on the bottom side of the substrate 330. Conducting traces (not shown) are provided in the substrate 330 to electrically connect the bond fingers on the top side to the solder balls 340 on the bottom side. Bonding wires 314 and 324 are attached between bonding pads (not shown) on the active surfaces of the chips and bonding fingers (not shown) on the top side of the substrate 330. Therefore, the bonding wires electrically connect the chips to the substrate 330. The connectivity between chips is achieved by connecting respective bond fingers in the substrate 330. However, it is also possible to make direct electrical connection between chips using bonding wires 316 to electrically connect respective bonding pads as shown in FIG. 3A. While solder balls 340 are used by the package for attaching the MCP to a circuit board or for further package integration, other means for electrically connecting the MCP to a circuit board or for further package integration may be used.

The MCP as shown in FIG. 3A may correspond to a non-volatile chip and one system processing chip for the capsule camera. The system processing chip may correspond to an integrated chip that incorporates all processing modules (sensor image processing module 220, motion evaluation module 230, image/video compression module 270 and system controller 290). The system processing chip may be larger than the non-volatile chip. In this case, the system chip is designated as the second chip 320 and the non-volatile chip is designated as the first chip. The system processing chip may be smaller than the non-volatile chip. In this case, the system chip is designated as the first chip 320 and the non-volatile chip is designated as the second chip. When an intra-frame image compression is adopted, such as JPEG, the buffer memory size may be small and the buffer memory may be embedded on the system processing chip. However, when inter-frame video compression is used, a larger size buffer may be required to store a full previously coded frame and a part of current frame. Accordingly, a separate memory device such as DRAM may be desirable for a capsule camera using inter-frame video coding. This frame buffer chip may also be stacked in the multi-chip package.

Figure 3B:
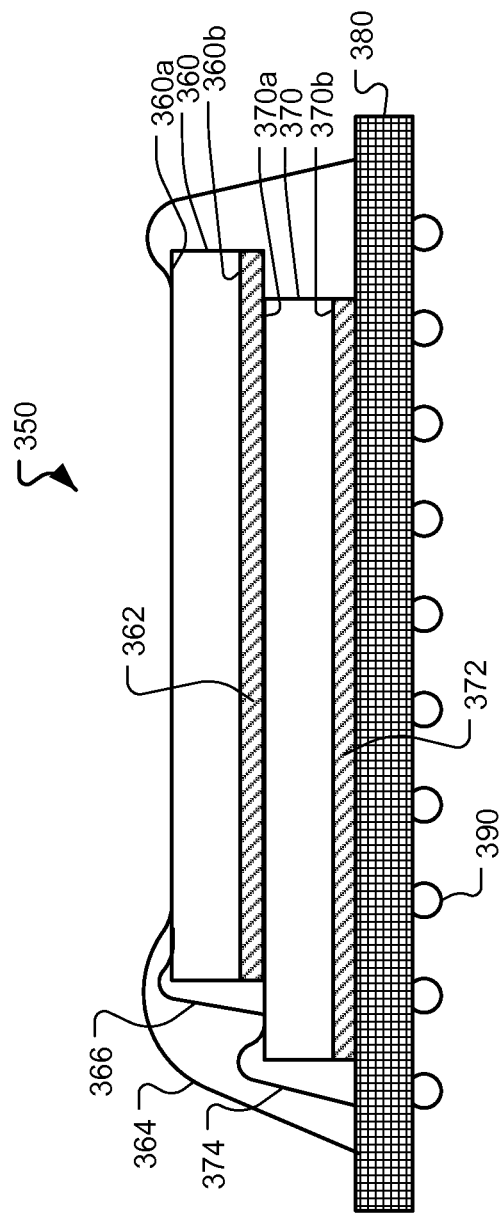
FIG. 3B illustrates another example of a stacked multiple chip package having two chips.

In the example shown in FIG. 3A, the difference in chip size is big enough to fabricate bonding pads on the un-covered area of the active surface of the second chip. When the chips have comparable sizes, alternative vertical stacking may be necessary. An alternative MCP 350 arrangement is shown in FIG. 3B where the first chip 360 has about the same size as the second chip 370. The first chip 360 is disposed on the top of the second chip 370 in a staggered arrangement, where one end of the first chip 360 overhangs from the second chip 370 so that some area of the circuit surface 370*a* of the second chip 370 will be exposed. Each chip has a circuit surface (360*a* and 370*a*) and a non-circuit surface (360*b* and 370*b*). The non-circuit surface of the first chip 360 is attached to the circuit surface 370*a* of the second chip 370 using die bonding layer 362. The circuit surface contains bonding pads (not shown in the drawing) that electrically connect internal circuits of the respective chip to external circuits. The non-circuit surface 370*b* of the second chip 370 is attached to the top side of substrate 380 using die bonding layer 372. Bonding wires 364 and 374 are used to electrically connect chips to the substrate. Bonding wires 366 may also be used between chips. Again, solder balls 390 are used by the package for attaching the MCP to a circuit board or for further package integration and other means for electrically connecting the MCP to a circuit board or for further package integration may be used. While two chips are stacked in the example of FIG. 3A, more than two chips could be stacked.

After chips are attached to the substrate and the bonding wires are connected, a process called encapsulation is applied to protect the bare dies and wires mechanically as well as chemically by filling the package with epoxy. There are several encapsulation techniques being practiced in the field such as dam molding, transfer molding, and glob-top. Upon the completion of the various manufacturing steps for MCP, the multiple bare chips are properly interconnected and packed into a single chip package. The MCP technique not only reduces the overall space, but also creates a very sturdy interconnection among the stacked chips. It helps to solve the space issue, particularly the vertical space issue associated with multiple chips required for the capsule camera with on-board storage.

The stacked MCP technology not only substantially reduces the physical dimension resulted from disposing the multiple chips on a final printed circuit board, but also substantially reduces the required connection on the board level. For example, a capsule camera with on-board storage may use a system processing chip having 44 bonding pads and two non-volatile memory chips having 28 pads each. If each chip is packed in a respective chip package and mounted on the printed circuit board, there will be roughly 100 connection nodes required on the printed circuit board for these three chips. However, a MCP encapsulating these three chips may result in a small number of contacts on the MCP. In one example, the MCP encapsulating these three chips has only 22 contacts (solder balls or pins) since the internal connections among the multiple chips have been connected within the MCP. Therefore, the MCP technology can substantially reduce the number of connection nodes on a board level and consequently reduces board space associated with routing traces among connection nodes.

While the MCP technology packs multiple chips into a single package intended for assembly in a final printed circuit board, the multiple chips may also be directly attached to the final printed circuit board. This assembly technology is called Chip-on-Board (COB) technology. The process of COB is very similar to the process of MCP. The COB process consists of attaching die, wire-bonding and encapsulation. Instead of using a chip carrier in the case of MCP, the chips are directly attached to the final printed circuit board for the COB assembly. While the chips are disposed on the final printed circuit board in a lateral arrangement in typical COB, two or more chips can be stacked vertically as well. Several vertical stacking arrangements to expose the bonding pads are described in FIGS. 3A-B. The same stacking means can be used for COB assembly as well. Furthermore, the COB assembly technology may also have chips mounted on both sides of the final printed circuit board. Therefore, besides MCP, the COB assembly technology is also useful to achieve compact vertical space associated with multiple chip packaging. A term "multiple chip assembly" is used to refer to both MCP and COB multiple chip packaging.

Figure 4:
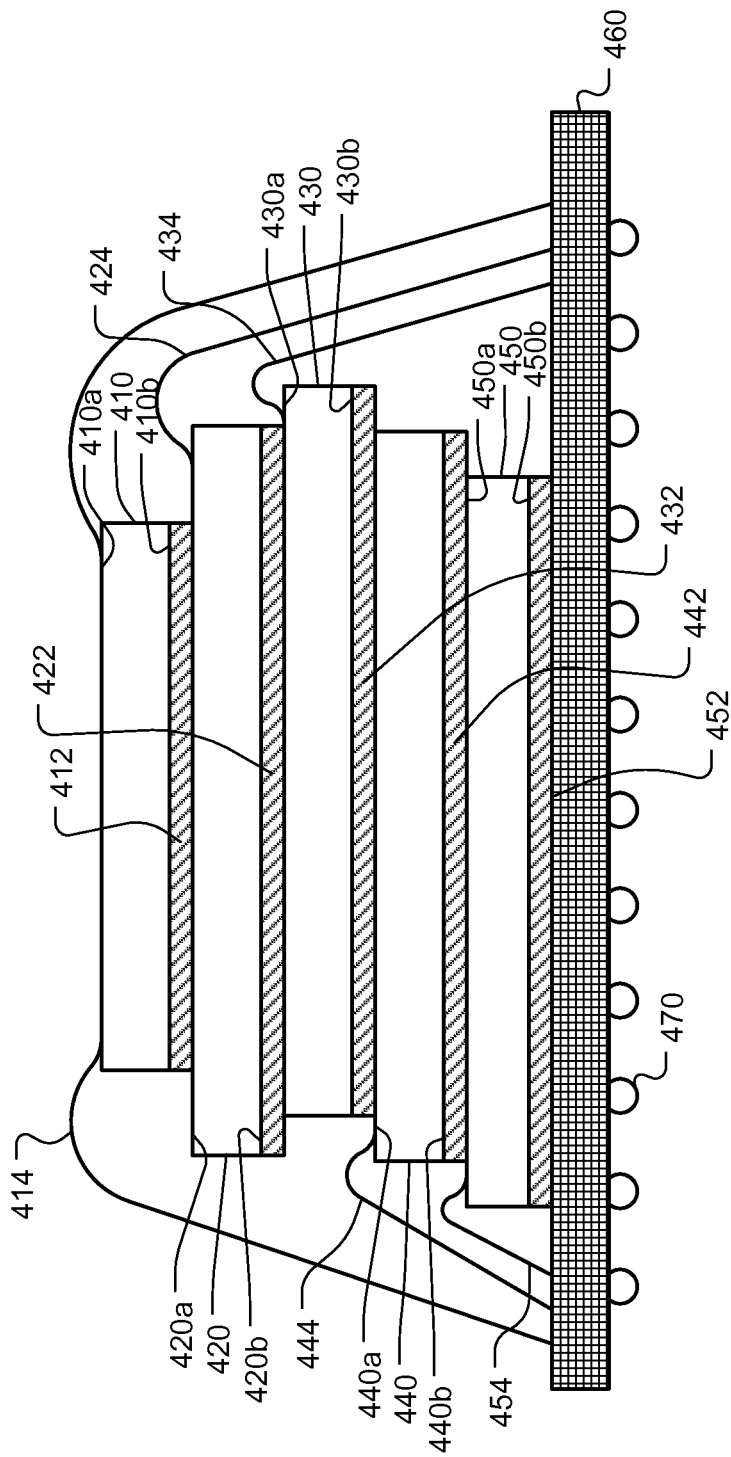
FIG. 4 illustrates an example of a stacked multiple chip package having five chips, where chips with about the same die size use staggered stacking to expose bonding pads.
Figure 5:
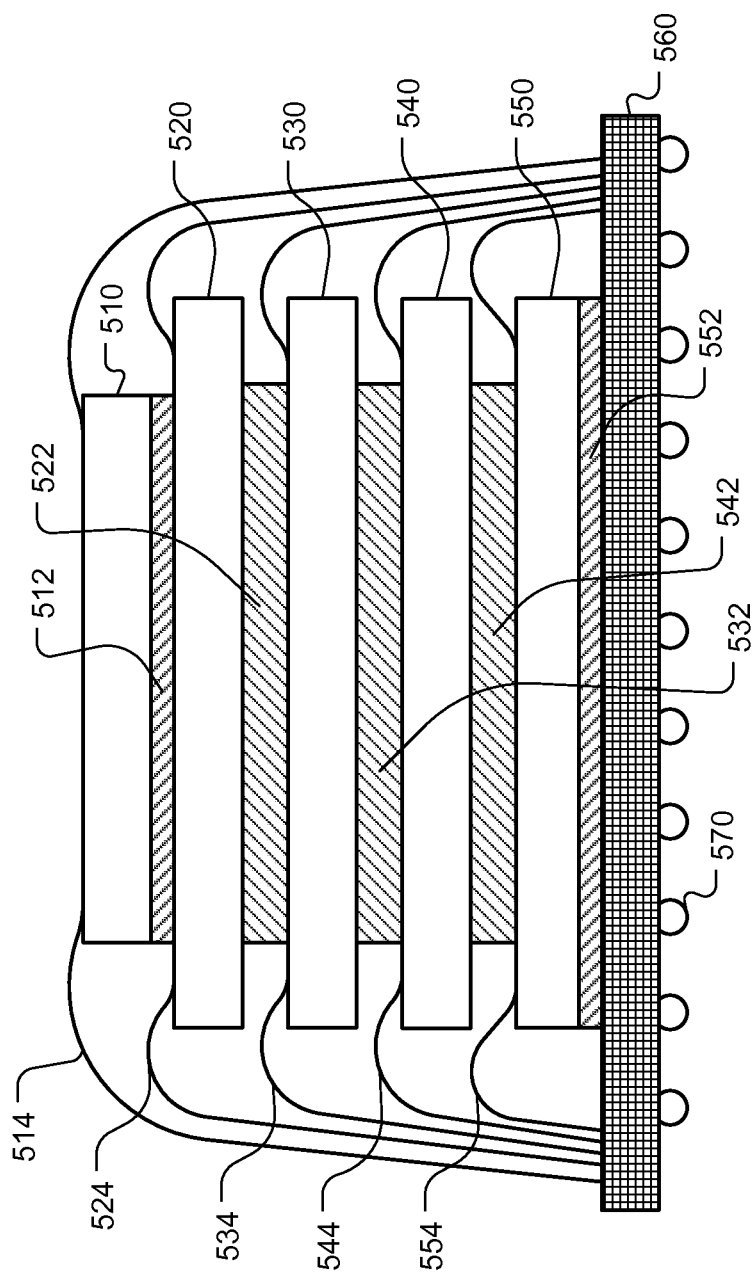
FIG. 5 illustrates another example of a stacked multiple chip package having five chips, where chips with about the same die size use spacers to expose bonding pads.

As mentioned earlier, depending on the required NVM capacity, multiple NVM chips may be required. The MCP technique can be applied to resolve the space issue. FIG. 4 illustrates an example of four vertical stacking NVM chips (420, 430, 440 and 450) with the system processing chip 410 on the top of the stacking NVM chips to form a single MCP 400. Each chip has a respective circuit surface (410a, 420a, 430a, 440a and 450a) and a non-circuit surface (410b, 420b, 430b, 440b and 450b). A die bonding layer (412, 422, 432, 442 and 452) is used to attach the respective chip on top of another chip or the substrate 460. Since the NVM chips have the same or similar size, the NVM chips (420, 430, 440 and 450) are stacked up vertically in a staggered arrangement so the each of these NVM chips will have an area in the circuit surface for exposing bonding pads fabricated on the circuit surface. Bonding wires 414, 424, 434, 444, and 454 are used to electrically connect the chips to the substrate. The connectivity between chips is achieved by electrically connecting respective bond fingers (not shown) in the substrate 460. However, it is also possible to make direct connection between chips using bonding wires to connect respective bonding pads. While solder balls 470 are used by the package for attaching the MCP to a circuit board or for further package integration, other means for connecting the MCP to a circuit board or for further package integration may be used. In the example shown in FIG. 4, the benefit of vertical space saving is very substantial because the large number of chips is packed into a single chip package. The examples in FIG. 3B and FIG. 4 illustrate a staggered vertical stacking means for chips with about the same size to expose areas of bonding pads. Others means for stacking chips with similar die sizes may also be used to expose bonding pads. FIG. 5 illustrate an alternative vertical stacking means for chips with similar sizes, where a spacer is used between two chip with similar sizes to expose areas for bonding pads. Chips 520, 530, 540 and 550 have about the same sizes and spacers 522, 532, and 542 are used between respective chips to expose areas for bonding pads. Bonding wires 514, 524, 534, 544 and 554 are used to electrically connect bonding pads on the chips to the bonding fingers on the substrate. Nevertheless bonding wires may also be used to electrically interconnect two chips directly. Similar to the examples in FIG. 3B and FIG. 4, a substrate 560 and solder balls 570 are used to interconnect the MCP to a printed circuit board or for further package integration. The spacer-based vertical stacking may have smaller footprint and may result in smaller package size. However, the spacer is thicker than a typical bonding layer (512 or 542) and the spacer-based vertical stacking MCP will result in a taller package.

In FIG. 4 and FIG. 5, the examples illustrate five chips being stacked up. While the multi-chip package can substantially reduce the vertical space compared with a conventional approach using individual chip packages, it may be desirable to further reduce the height of the multiple chip assembly. For example, it may be desirable to keep the height of multi-chip package around 1 mm or less. The thickness of regular wafer may be over 200 μm. The heights of wafers, thickness of the bonding layers, the substrate thickness, the solder ball height and height of encapsulation material over the chip on the top may easily exceed the desirable MCP height. Therefore the wafers may have to be thinned to reduce the overall MCP or COB height. The wafer can be thinned chemical-mechanically to result in dies with thickness less than 100 μm or even 50 μm according to current technology. The die can be further thinned to as little as 10 μm if necessary. Depending on desirable MCP or COB height, one or more of the multiple chips can be thinned properly.

While the MCP examples illustrated in FIGS. 3A-B, 4 and 5 use bonding wires to electrically interconnect chips and substrate, other interconnection means may also be used.

Figure 6:
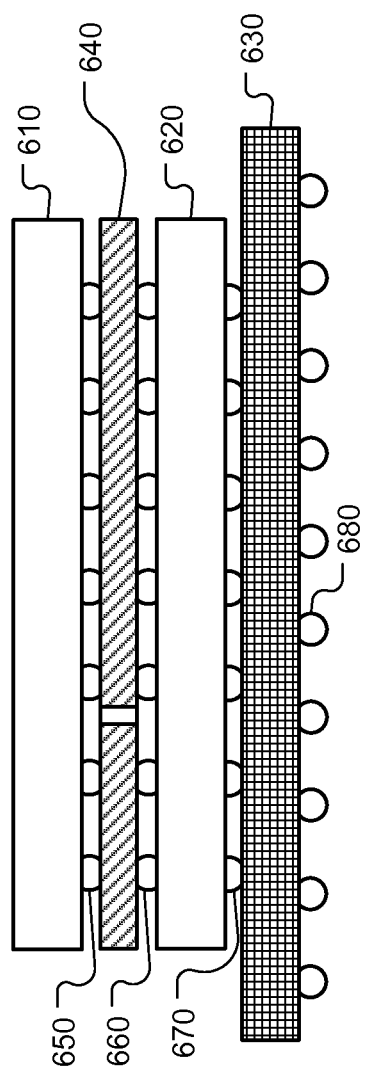
FIG. 6 illustrates another example of a stacked multiple chip package, where a second substrate is used to electrically interconnection between chips.

FIG. 6 illustrates an example of stacked MCP with 2 chips, where ball bumps 650, 660 and 670 are used to electrically interconnect chips 610 and 620 and substrate 630. A second substrate 640 having connection pads on both sides of the substrate 640 to electrically interconnect chip 610 and chip 620. As before, solder balls 680 are attached to the bottom side of the substrate 630.

Figure 7A:
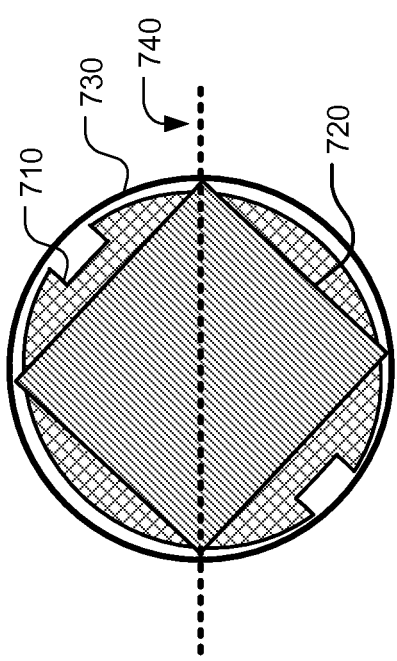
FIGS. 7A-B illustrate an example of PCB arrangement where the MCP has a diagonal dimension substantially the same as the capsule inner diameter.
Figure 7B:
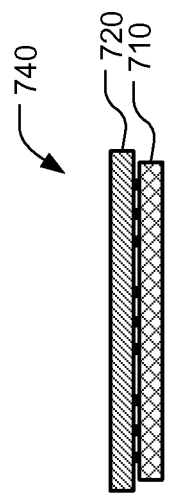

In some cases, the MCP may have a diagonal dimension that is almost the same as the capsule inner diameter. On the other hand, the PCB has to be smaller to fit into the capsule. In typical PCB arrangement, the chip footprint is always within the PCB boundary. Therefore, the PCB arrangement according to a conventional approach will not work for such cases. Accordingly, a means for solving the size issue is disclosed herein for fitting a MCP having a diagonal dimension almost the same as the capsule inner diameter. Since there are tolerances on part and board sizes and also the registration between the two, the PCB has to be smaller than the capsule inner diameter by an amount equal to or greater than the tolerance stack up, otherwise the combination of MCP and PCB would no longer fit into the capsule. FIG. 7A illustrates a top view of such case where the PCB 710 fits into the inner diameter of the capsule camera housing 730. The MCP 720 has a diagonal dimension that is almost the same as the capsule inner diameter. A cross section view at location 740 is shown in FIG. 7B where the corners of the MCP are slightly overhung from the PCB 710.

The present invention of a capsule camera with on-board storage has been described above using several examples. The capsule camera packs image sensor, light source, battery, stacked multi-chip assembly into a housing adapted to be swallowed. The stacked multi-chip assembly comprises one or more non-volatile memory chip to store the captured images and at least one processing chip where the at least one processing chip comprises compression module to perform image or video compression. The stacked multi-chip assembly may be based on the MCP technology where a chip carrier is used for disposing the chips vertically. The stacked multi-chip assembly may be based on the COB technology where a final printed circuit board is used for mounting the chips vertically. The final printed circuit board can be a rigid board or a flex board. Furthermore, the flex board may also include flex cable extended from the flex board.

Numerous modifications and variations within the scope of the invention are possible. While the invention has been described by way of example and in terms of a preferred embodiment, it is to be understood that the invention is not limited thereto. On the contrary, it is intended to cover various modifications and similar arrangements and procedures

What is claimed is:

1. A capsule camera apparatus having on-board storage, comprising:
 a housing adapted to be swallowed, said housing enclosing:
  a light source to illuminate lumen walls;
  an image sensor to provide image data;
  a battery to provide power to the capsule camera;
  a system processing chip comprising a compression module to perform image or video compression on the image data and to provide compressed data; and
  one or more non-volatile memory chips stores the compressed data;
  wherein the system processing chip and said one or more non-volatile memory chips are stacked on an assembly piece vertically and the assembly piece is a chip carrier using a substrate;
  wherein the system processing chip and said one or more non-volatile memory chips are electrically interconnected with the assembly piece; and
  wherein a portion of the chip carrier extends from a printed circuit board, wherein the chip carrier is disposed on the printed circuit board.

2. The capsule camera apparatus of claim 1, wherein said one or more non-volatile memory chips comprises at least two non-volatile memory chips.

3. The capsule camera apparatus of claim 1, wherein one or more of the system processing chip and said one or more non-volatile memory chips are thinned.

4. The capsule camera apparatus of claim 1, wherein the system processing chip and said one or more non-volatile memory chips are electrically interconnected with the assembly piece using bonding wires.

5. The capsule camera apparatus of claim 1, wherein at least two of the system processing chip and said one or more non-volatile memory chips are electrically interconnected with each other using bonding wires.

6. The capsule camera apparatus of claim 1, wherein at least two of the system processing chip and said one or more non-volatile memory chips are electrically interconnected with the assembly piece using solder bumps.

7. The capsule camera apparatus of claim 1, wherein at least two of the system processing chip and said one or more non-volatile memory chips are interconnected with each other using a second substrate.

8. The capsule camera apparatus of claim 1, wherein said one or more non-volatile memory chips comprises at least two non-volatile memory chips, and wherein at least two of the system processing chip and said at least two non-volatile memory chips are stacked in staggered arrangement to expose solder pads on said at least two of the system processing chip and said at least two non-volatile memory chips.

9. The capsule camera apparatus of claim 1, wherein said one or more non-volatile memory chips comprises at least two non-volatile memory chips, and wherein at least two of the system processing chip and said at least two non-volatile memory chips are stacked with a spacer in between to expose solder pads on said at least two of the system processing chip and said at least two non-volatile memory chips.

10. The capsule camera apparatus of claim 1, wherein at least two of the system processing chip and said one or more non-volatile memory chips are stacked on both sides of the assembly piece with the system processing chip and said one or more non-volatile memory chips vertically overlapping.

11. The capsule camera apparatus of claim 1, further comprising a frame buffer memory chip electrically interconnected with the assembly piece, wherein the frame buffer memory chip, the system processing chip and said one or more non-volatile memory chips are stacked on the assembly piece vertically.

12. The capsule camera apparatus of claim 11, wherein said one or more non-volatile memory chips comprises at least two non-volatile memory chips.

13. The capsule camera apparatus of claim 11, wherein one or more of the frame buffer memory chip, the system processing chip and said one or more non-volatile memory chips are thinned.

14. The capsule camera apparatus of claim 11, wherein the frame buffer memory chip, the system processing chip and said one or more non-volatile memory chips are electrically interconnected with the assembly piece using bonding wires.

15. The capsule camera apparatus of claim 11, wherein at least two of the frame buffer memory chip, the system processing chip and said one or more non-volatile memory chips are electrically interconnected with each other using bonding wires.

16. The capsule camera apparatus of claim 11, wherein at least two of the frame buffer memory chip, the system processing chip and said one or more non-volatile memory chips are electrically interconnected with the assembly piece using solder bumps.

17. The capsule camera apparatus of claim 11, wherein at least two of frame buffer memory chip, the system processing chip and said one or more non-volatile memory chips are interconnected with each other using a second substrate.

18. The capsule camera apparatus of claim 11, wherein said one or more non-volatile memory chips comprises at least two non-volatile memory chips, and wherein at least two of the frame buffer memory chip, the system processing chip and said one or more non-volatile memory chips are stacked in staggered arrangement to expose solder pads on said at least two of the frame buffer memory chip, the system processing chip and said one or more non-volatile memory chips.

19. The capsule camera apparatus of claim 11, wherein said one or more non-volatile memory chips comprises at least two non-volatile memory chips, and wherein at least two of the frame buffer memory chip, the system processing chip and said one or more non-volatile memory chips are stacked with a spacer in between to expose solder pads on said at least two of the frame buffer memory chip, the system processing chip and said one or more non-volatile memory chips.

20. The capsule camera apparatus of claim 11, wherein at least two of the frame buffer memory chip, the system processing chip and said one or more non-volatile memory chips are stacked on both sides of the assembly piece with the frame buffer memory chip, the system processing chip and said one or more non-volatile memory chips vertically overlapping.

21. The capsule camera apparatus of claim 1, wherein the compression module is configured for motion-compensated video compression.

22. The capsule camera apparatus of claim 1, wherein said one or more non-volatile memory chips are based on flash memory.

23. The capsule camera apparatus of claim 1, wherein the chip carrier has diagonal dimension substantially the same as an inner diameter of the housing.

24. A capsule camera apparatus having on-board storage, comprising:
a housing adapted to be swallowed, said housing enclosing:
a light source to illuminate lumen walls;
an image sensor to provide image data;
a battery to provide power to the capsule camera;
a system processing chip comprising a compression module to perform image or video compression on the image data and to provide compressed data and a light control module to control the light source; and
one or more non-volatile memory chips stores the compressed data;
wherein the system processing chip and said one or more non-volatile memory chips are stacked on an assembly piece vertically;
wherein the system processing chip and said one or more non-volatile memory chips are electrically interconnected with the assembly piece; and
wherein the light control module receives a light control signal from a system controller in the system processing chip to synchronize the light source with operations of image sensor.

25. A capsule camera apparatus having on-board storage, comprising:
a housing adapted to be swallowed, said housing enclosing:
a light source to illuminate lumen walls;
an image sensor to provide image data;
a battery to provide power to the capsule camera;
a system processing chip comprising a compression module to perform image or video compression on the image data and to provide compressed data; and
a non-volatile memory chip to store both the compressed data and boot-up codes or program codes associated with a system controller in the system processing chip;
wherein the system processing chip and the non-volatile memory chip are stacked on an assembly piece vertically; and
wherein the system processing chip and the non-volatile memory chip are electrically interconnected with the assembly piece.

* * * * *